US006455564B1

(12) United States Patent
Meglasson et al.

(10) Patent No.: US 6,455,564 B1
(45) Date of Patent: Sep. 24, 2002

(54) METHOD OF TREATING SEXUAL DISTURBANCES

(75) Inventors: Martin Durham Meglasson, Kalamazoo, MI (US); Robert B. McCall, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/465,668

(22) Filed: Dec. 17, 1999

Related U.S. Application Data

(60) Provisional application No. 60/120,543, filed on Feb. 17, 1999, provisional application No. 60/115,922, filed on Jan. 14, 1999, provisional application No. 60/115,051, filed on Jan. 8, 1999, and provisional application No. 60/114,840, filed on Jan. 6, 1999.

(51) Int. Cl.$^7$ ............................................. A61K 31/415
(52) U.S. Cl. ..................................................... 514/387
(58) Field of Search .......................................... 514/387

(56) References Cited

U.S. PATENT DOCUMENTS

| | | |
|---|---|---|
| 4,127,118 A | 11/1978 | Latorre |
| 4,801,587 A | 1/1989 | Voss et al. |
| 5,250,534 A | 10/1993 | Bell et al. |
| 5,273,975 A * | 12/1993 | Moon et al. |
| 5,541,211 A | 7/1996 | Pertovaara et al. |
| 5,770,606 A | 6/1998 | El-Rashidy et al. |
| 5,773,020 A | 6/1998 | Place et al. |

FOREIGN PATENT DOCUMENTS

WO   WO94/282902   12/1994   ......... A61K/31/505

OTHER PUBLICATIONS

*International Journal of Impotence Research*, 10 (Supplement 3), Aug. 1998, Abstracts #417 and 419.

*Brain Research*, 55,383–389 (1973).

Diagnostic and Statistical Manual of Mental Disorders, Fourth Edition, (DSM–IV), American Psychiatric Association, Washington DC (1994).

DSM–IV Guidebook, American Psychiatric Press, Inc., Washington DC 1995.

* cited by examiner

*Primary Examiner*—Russell Travers
*Assistant Examiner*—San-ming Hui
(74) *Attorney, Agent, or Firm*—Bruce Stein

(57) ABSTRACT

The present invention is a method of treating sexual disturbances in humans and inducing mating in non-human mammals using the compounds of formula (A)

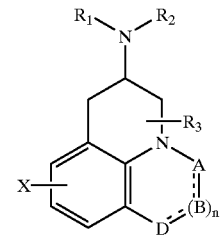

in a dosage range where the sexually therapeutic amount is from about 0.2 thru 8 mg/person/dose and where the sexually mating amount is from about 0.003 thru 0.2 mg/kg/dose.

14 Claims, No Drawings

METHOD OF TREATING SEXUAL DISTURBANCES

CROSS REFERENCE TO RELATED APPLICATIONS

This application claims the benefit of the following provisional applications: U.S. Ser. No. 60/120,543, filed Feb. 17, 1999; U.S. Ser. No. 60/115,922, filed Jan. 14, 1999; U.S. Ser. No. 60/115,051, filed Jan. 8, 1999; and U.S. Ser. No. 60/114,840, filed Jan. 6, 1999, under 35 USC §119(e)(1).

FIELD OF THE INVENTION

The present invention is a method of treating sexual disturbances using the compounds of U.S. Pat. No. 5,273,975.

DESCRIPTION OF THE RELATED ART

There are a number of diseases/conditions which directly affect the sexual lives of humans and animals. These include orgasmic disorders, lack of interest in sex and erectile dysfunction in males. In addition there are a number of diseases/conditions which indirectly affect the sexual lives of humans. There are a few pharmaceutical agents to treat this diseases/conditions and others in clinical development.

U.S. Pat. No. 5,273,975 discloses that the compounds (A) of the present invention are useful to stimulate sexual activity and to alleviate impotence. The useful dosage range disclosed in U.S. Pat. No. 5,273,975 is "at least 10 mg up to about 1200 mg per day". The operable dosage range in the present invention is considerably lower. The compounds of U.S. Pat. No. 5,273,975 have been used in clinical trials to prove their usefulness in treating Parkinson's disease at a dose of 30 mg/person. Compounds (A) of the present invention are used at a dose of less than 8 mg in treating the sexual disturbances of the present invention. U.S. Pat. No. 5,273,975 generically discloses compounds where the variable substituent "A" can be either a carbonyl group (—CO—) or a thiocarbonyl (—CS—).

U.S. Pat. No. 5,250,534 discloses sildenafil (VIAGRA®). The compounds (A) of the present invention are quite different chemically than sildenafil. International Publication WO94/282902 discloses the use of sildenafil for treating male impotence.

U.S. Pat. No. 4,127,118 discloses the intracavemosal injection of a vasodilator for enhancing an erection of the penis. PGE1 is a vasodilator and is sold as CAVERJECT® to treat male erectile dysfunction. The compounds (A) of the present invention are not prostaglandins and are not injected into the penis.

International Journal of Impotence Research, 10 (Supplement 3), August 1998, Abstracts #417 and 419 disclose that apomorphine, which is available in a number of countries to treat Parkinson's Disease, is in late-stage development as a sublingual formulation for treating male erectile dysfunction. The compounds (A) used in the present invention are not apomorphine analogs. U.S. Pat. No. 5,770,606 discloses sublingual use of apomorphine for treating erectile dysfunction.

U.S. Pat. No. 5,541,211 discloses that yohimbine can be used to treat erectile dysfunction. The compounds of formula (A) are quite different chemically as compared to yohimbine.

U.S. Pat. No. 4,801,587 discloses that phentolamine (VASOMAX®) which is available in a number of countries for treating hypertension is also useful for treating erectile dysfunction. The compounds of formula (A) are quite different chemically as compared to phentolamine. In addition, the compounds of formula (A) are not applied either topically to the penis nor intra-urethrally.

U.S. Pat. No. 5,773,020 discloses that intraurethral PGE1 (MUSE) is useful for treating erectile dysfunction. Compounds (A) are not prostaglandins and are not administered intraurethrally.

*Brain Research*, 55, 383–389 (1973) reports on the sexually stimulating effect of L-DOPA given to male rats and conjuctures that it may be the reason that hypersexuality occasionally is seen in patients with Parkinson's syndrome during L-DOPA treatment.

SUMMARY OF INVENTION

Disclosed is a method of treating sexual disturbances in a human who is in need of such treatment which comprises administering a sexually therapeutically effective amount of a compound of the formula (A)

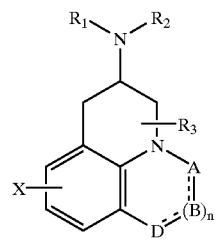

where $R_1$, $R_2$ and $R_3$ are the same or different and are: —H, $C_1$–$C_6$ alkyl, $C_3$–$C_5$ alkenyl, $C_{3-C5}$ alkynyl, $C_3$–$C_5$ cycloalkyl, $C_4$–$C_{10}$ cycloalkyl, phenyl substituted $C_1$–$C_6$ alkyl, —$NR_1R_2$ where $R_1$ and $R_2$ are cyclized with the attached nitrogen atom to produce pyrrolidiyl, piperidinyl, morphoninyl, 4-methyl piperazinyl or imidazolyl;

X is: —H, $C_1$–$C_6$ alkyl, —F, —Cl, —Br, —I, —OH, $C_1$–$C_6$ alkoxy, cyano, carboxamide, carboxyl, ($C_1$–$C_6$ alkoxy)carbonyl;

A is: CH, $CH_2$, CH-(halogen) where halogen is —F, —Cl, —Br, -I, $CHCH_3$, C=O, C=S, C—$SCH_3$, C=NH, C—$NH_2$, C—$NHCH_3$, C—$NHCOOCH_3$, C—NHCN, $SO_2$, N;

B is: $CH_2$, CH, CH-(halogen) where halogen is as defined above, C=O, N, NH, N—$CH_3$, D is: CH, $CH_2$, CH-(halogen) where halogen is as defined above, C=O, O, N, NH, N—$CH_3$; and n is 0 or 1, and where ～～ is a single or double bond, with the provisos:

(1) that when n is 0, and
   A is $CH_2$, CH-(halogen) where halogen is as defined above, $CHCH_3$, C=O, C=S, C=NH, $SO_2$,; then
   D is $CH_2$, CH-(halogen) where halogen is as defined above, C=O, O, NH, N—$CH_3$;

(2) that when n is 0, and
   A is CH, C—$SCH_3$, C—$NH_2$, C—$NHCH_3$, C—$NHCOOCH_3$, C—NHCN, N; then
   D is CH, N;

(3) that when n is 1, and
   A is $CH_2$, CH-(halogen) where halogen is as defined above, $CHCH_3$, C=O, C=S, C=NH, $SO_2$; and B is CH$_2$, CH—(halogen) where halogen is as defined above, C=O, NH, N—CH$_3$; then D is CH$_2$, C=O, O, NH, N—CH$_3$;

(4) that when n is 1, and

A is CH, C—SCH$_3$, C—NH$_2$, C—NHCH$_3$, C—NHCOOCH$_3$, C—NHCN, N; and

B is CH, N; then

D is CH$_2$, C=O, O, NH, N—CH$_3$;

(5) that when n is 1, and

A is CH$_2$, CHCH$_3$, C=O, C=S, C=NH, SO$_2$, and

B is CH, N; then

D is CH, N; and pharmaceutically acceptable salts thereof to the human.

Also disclosed is a method of inducing mating a non-human mammal which comprises administering a sexually mating amount of a compound of the formula (A) and pharmaceutically acceptable salts thereof.

Further disclosed is a method of treating a sexual deficiency state in a human who has epilepsy, craniopharyngioma, hypogonadism or who has had a hysterectomyoophorectomy, hysterectomy or oophorectomy which comprises administering a sexually therapeutically effective amount of a compound of the formula (A) and pharmaceutically acceptable salts thereof.

Additionally disclosed is a method of increasing sexual desire, interest or performance in a human who is desirous thereof which comprises administering a sexually useful effective amount of a compound of the formula (A) and pharmaceutically acceptable salts thereof.

Disclosed is (5R)-5-(methylamino)-5,6-dihydro-4H-imidazo[4,5,1-ij]quinoline-2(1H)-thione and pharmaceutically acceptable salts thereof.

DETAILED DESCRIPTION OF THE INVENTION

The present invention includes four separate methods of treating sexual problems. First, it is a method of treating sexual disturbances in a human who is in need of such treatment which comprises administering a sexually therapeutic amount of a compound of the formula (A) and its pharmaceutically acceptable salts. Second, it includes a method of inducing mating a non-human mammal which comprises administering a sexually mating amount of a compound of the formula (A) and pharmaceutically acceptable salts thereof. Thirdly, it includes a method of treating a sexual deficiency state in a human who has a disease/condition the primary pathology of which does not relate to sexual disfunction, but indirectly produces reduced sexual functioning. The diseases/conditions which can produce this type of sexual disfunction include epilepsy, craniopharyngioma, hypogonadism or who has had a hysterectomyoophorectomy, hysterectomy or oophorectomy. Fourthly, there are individuals who do not appear to have any sexual disturbance or disease/condition which will produced an adverse effect on their sexual lives, but none the less wish to increase their sexual desire, interest or sexual performance and who will benefit by use of the compounds of formula (A).

The compounds of formula (A), and pharmaceutically acceptable salts, which are useful in the method of treatment of the present invention are known, see U.S. Pat. No. 5,273,975. It is preferred that the pharmaceutically acceptable salt is selected from the group consisting of salts of the following acids methanesulfonic, hydrochloric, hydrobromic, sulfuric, phosphoric, nitric, benzoic, citric, tartaric, fumaric, maleic, CH$_3$—(CH$_2$)$_n$—COOH where n is 0 thru 4, HOOC—(CH$_2$)$_N$—COOH where n is as defined above. It is preferred that the compound of formula (A) have n be 0, A be C=O and D be NH. It is more preferred that the compound of formula (A) be either (5R)-(methylamino)-5,6-dihydro-4H-imidazo[4,5,1-ij]quinolin-2(1H)-one or (5R)-5-(methylamino)-5,6-dihydro-4H-imidazo[4,5,1-ij]quinoline-2(1H)-thione. It is more preferred that the compound of formula (A) be (5R)-(methylamino)-5,6-dihydro-4H-imidazo[4,5,1-ij]quinolin-2(1H)-one (Z)-2-butenedioate (1:1).

A preferred process to produce the preferred compounds within the scope of the compounds of formula (A) is set forth in PREPARATION 1 and the numerical EXAMPLEs as well as CHART A.

Non-human mammals include commercial animals (horses, cattle, swine, sheep and transgenic mice) and zoo animals (panda bears, elephants, zebras, lions, tigers, monkeys and apes), sporting animals (horses and dogs) as well as domesticated animals (dogs and cats). The humans and non-human mammals both be either a male or female.

The sexual disturbances in humans treated by the present invention include hypoactive sexual desire disorder, female sexual arousal disorder, male erectile disorder, female orgasmic disorder and male orgasmic disorder. The sexual disturbances of the present invention are known to those skilled in the art and are adequately described for a medical practitioner. In particular, see Diagnostic and Statistical Manual of Mental Disorders, Fourth Edition, (DSM-IV), American Psychiatric Association, Washington D.C., 1994 as well as the DSM-IV Guidebook, American Psychiatric Press, Inc., Washington D.C., 1995.

When inducing mating in the non-human mammals it is desirable to treat one member of the mating pair in some cases. This is most likely to be the situation where previous attempts at mating the pair have failed and one member of the pair is not known to have prior offspring. In that case, this member would be advantageously treated. In other cases, it may be desirable to treat both the male and female prior to the anticipated mating. The latter is most likely to be advantageous when the intended mating is between sexually inexperienced animals and prior attempts at mating the pair have failed.

The compounds of formula (A) are also useful in treating humans whose primary disease, condition or situation is not one of sexual disfunction, but rather the primary disease or condition leads to a secondary clinical situation where the human (male or female) experiences diminished sexual desire, interest and/or function. These diseases include epilepsy, craniopharyngioma, hypogonadism or who has had a hysterectomyoophorectomy, hysterectomy or oophorectomy and can produce a sexual deficiency state which is treated in the same way as those individuals who have one or more of the five sexual disturbances identified above. The sexually therapeutic effective amount is the same and is administered in the same way by the same routes of administration as for those humans who have sexual disturbances.

The compounds of formula (A) are also useful in increasing sexual desire, interest or performance in individuals who do not have any of the five sexual disturbances nor any of the following diseases or conditions, epilepsy, craniopharyngioma, hypogonadism or who has had a hysterectomyoophorectomy, hysterectomy or oophorectomy. These individuals are treated the same way as those having any of the five sexual disturbances. The sexually useful effective amount to be used here is the same as the sexually therapeutically effective amount for those with sexual disturbances. The sexually useful therapeutically effective amount is administered in the same way by the same routes of administration as for those humans who have sexual disturbances.

In (1) treating the sexual disturbances of humans, (2) inducing mating of non-human mammals, (3) treating humans whose primary disease or condition leads to a secondary clinical situation where the human experiences diminished sexual desire, interest and/or function and (4) increasing the sexual desire, interest or performance in individuals who do not have any of the above problems the compounds of formula (A) in the known appropriate pharmaceutical dosage form for a given route of administration may be administered orally, intra-nasally, buccally, intra-pulmonary, parenterally and rectally. For treating humans, it is preferred that the compound of formula (A) be administered orally, intra-nasally, buccally and intra-pulmonarlly; it is more preferred that the compounds of formula (A) be administered orally. For treating non-human mammals, it is preferred that the compounds of formula (A) be administered orally, parenterally and rectally; it is more preferred that the compounds of formula (A) be administered orally.

The operable sexually therapeutic effective amount as well as the operable sexually useful effective amount of the compounds of formula (A) is from about 0.2 thru about 8 mg/person/dose. It is preferred that the sexually therapeutic effective amount and sexually useful effective amount is from about 0.5 thru about 5 mg/person/dose. It is more preferred that the sexually therapeutic effective amount and sexually useful effective amount is from about 1 thru about 3 mg/person/dose. If doses less than this are used the desired effect will not be obtained. If doses greater than this are used, undesirable side effects occur and the desired effect will not be obtained. The term "therapeutic" is used in treating a disease or condition; the term "useful" is used when treating humans who do not have one of the above diseases or conditions which cause sexual dysfunction but who are considered normal and who wish to increase their sexual desire, interest or performance.

The operable sexually mating amount of the compounds of formula (A) is from about 0.003 thru about 0.2 mg/kg/dose. It is preferred that the sexually mating amount is from about 0.01 thru about 0.125 mg/kg/dose. It is more preferred that the sexually mating amount is from about 0.025 thru about 0.075 mg/kg/dose.

To obtain the desired effect in humans, the sexually therapeutic effective amount or sexually useful effective amount of the compounds of formula (A) should be administered from about 10 minutes to about 8 hr prior to sexual activity. It is preferred that the compounds of formula (A) be administered from about 0.5 hr to about 1 hr prior to sexual activity. It is more preferred that the compounds of formula (A) be administered about 0.5 hr prior to sexual activity. Sexual activity includes sexual intercourse with or without orgasm, ejaculation, masturbation and sexual foreplay.

To obtain the desired mating effect in non-human mammals, the compounds of formula (A) is administered from about 10 minutes to about 8 hr prior to mating. It is preferred that the compounds of formula (A) be administered from about 10 minutes to about 1 hr prior to mating. It is more preferred that the compounds of formula (A) be administered from about 10 minutes to about 0.5 hr prior to mating.

It is preferred that the humans do not have Parkinson's disease.

It is preferred that the in humans administration of the compounds of formula (A) does not produce postural hypotension.

The present invention is further illustrated by EXAMPLES A–P.

The exact dosage of the compounds of formula (A) which are useful in the four methods of this invention depends on the route of administration, the particular compound used, the particular condition being treated, the severity of the condition being treated, the age, weight, general physical condition of the particular patient, other medication the individual may be taking as is well known to those skilled in the art and can be more accurately determined by measuring the blood level or concentration of the compound and/or metabolite in the patient's blood and/or the patient's response to the particular condition being treated.

The compounds of formula (A) can also be used with other agents in (1) treating the five sexual disturbances, (2) in inducing mating of a non-human mammal, (3) in treating a sexual deficiency state in humans who have one or more of the following diseases/conditions—epilepsy, craniopharyngioma, hypogonadism or who has had a hysterectomyoophorectomy, hysterectomy or oophorectomy or (4) increasing sexual desire, interest or performance in a human who does not have any sexual disturbance or one of the above diseases/conditions. It is known that vascular smooth muscle relaxation is necessary for vascular engorgement of the penis and the clitoris during normal male and female sexual behavior and that agents which promote vascular engorgement of the penis and clitoris are useful in enhancing sexual motivation, desire and performance. Agents which effectuate vascular smooth muscle relaxation include phosphodiesterase type 5 inhibitors, such as sildenafil (Viagra) and ICOS-351; phosphodiesterase type 3 inhibitors, such as milrinone; non-selective phosphodiesterase inhibitors such as papaverine; nitric oxide donor drugs such as linsidomine; alpha type 1 adrenergic receptor antagonists such as phentolamine produce relaxation of vascular smooth muscle from human penis in the presence of norepinephrine; alpha type 2 adrenergic receptor antagonists such as yohimbine; prostaglandin E1 receptor agonists such as PGE1 (CAVERJECT™ Injection and MUSE™); as well as vasoactive intestinal polypeptide (VIP) agents.

These vascular smooth muscle relaxation agents are administered by oral, parenteral, buccal, rectal, intranasal, intrapulmonary, intraurethral or topical routes. The preferred route of administration will depend on the specific properties of the drug(s) to be combined with the compound(s) of formula (A). The preferred route of administration for a phosphodiesterase type 3 or 5 receptor inhibitor and an alpha type 1 or 2 adrenergic receptor inhibitor is oral. The preferred route of administration for a prostaglandin E receptor agonist, nitric oxide donor, non-specific phosphodiesterase inhibitor, and VIP is intracavemosal injection or intraurethral topical administration in male mammals or topical administration to the vulva in the female.

The dose of some of the vascular smooth muscle relaxation agents is known to those skilled in the art, especially for sildenafil (VIAGRA™ Tablets), PGE1 (CAVERJECT™ Injection and MUSE™). For yohimbine the dose is about 1 to about 10 mg orally and can be given about three or four times daily as a routine. For phentolamine the dose is about 2 to about 40 mg orally or by bucal patch or about 0.5 to about 5 mg when given by intracavemosal injection. For papaverine the dose is about 4 to about 20 mg given by intracavemosal injection. For VIP the dose is about 5 to about 60 mg when given by intracavemosal injection.

When the compounds of formula (A) are used in conjunction with the vascular smooth muscle relaxation agents the compounds of formula (A) should be administered within the time frame discussed above. The sexually effective time period for administration of the vascular smooth muscle relaxation agents is well known for sildenafil (VIAGRA™ Tablets), PGE1 (CAVERJECT™ Injection and MUSE™). The sexually effective time period for administration of yohimbine is about 0 to about 4 hours before sexual activity; for phentolamine it is about 0 to about 4 hours prior to sexual activity when given orally or buccally and about 0 to about 2 hours when given by intracavemosal injection; for papaverine and VIP it is about 0 to about 2 hours prior to sexual activity.

When used in combination, the preferred combinations are (5R)-(methylamino)-5,6-dihydro-4H-imidazo[4,5,1-ij]quinolin-2(1H)-one and sildenafil, (5R)-(methylamino)-5,6-dihydro-4H-imidazo[4,5,1 -ij]quinolin-2(1H)-one and PGE1, (5R)-5-(methylamino)-5,6-dihydro-4H-imidazo[4,5,1-ij]quinoline-2(1H)-thione and sildenafil or (5R)-5-(methylamino)-5,6-dihydro-4H-imidazo[4,5,1-ij]quinoline-2(1H)-thione and PGE1.

Definitions and Conventions

The definitions and explanations below are for the terms as used throughout this entire document including both the specification and the claims.

I. Conventions for Formulas and Definitions of Variables

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1C_3$" refers only to the carbon atom content of the alkoxy group. Similarly while both $C_2$–$C_6$ alkoxyalkyl and ($C_1$–$C_3$)alkoxy ($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. Definitions

All temperatures are in degrees Centigrade.

TLC refers to thin-layer chromatography.

HPLC refers to high pressure liquid chromatography.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

NMR refers to nuclear (proton) magnetic resonance spectroscopy, chemical shifts are reported in ppm (δ) downfield from tetramethylsilane.

CMR refers to C-13 magnetic resonance spectroscopy, chemical shifts are reported in ppm (δ) downfield from TMS.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable anion salts include salts of the following acids methanesulfonic, hydrochloric, hydrobromic, sulfuric, phosphoric, nitric, benzoic, citric, tartaric, fumaric, maleic, $CH_3$—$(CH_2)_n$—COOH where n is 0 thru 4, HOOC—$(CH_2)_N$—COOH where n is as defined above.

(Z)-2-butenedioate refers to maleate.

When solvent pairs are used, the ratios of solvents used are volume/volume (v/v).

When the solubility of a solid in a solvent is used the ratio of the solid to the solvent is weight/volume (wt/v).

Sexual disturbance refers to hypoactive sexual desire disorder, female sexual arousal disorder, male erectile disorder, female orgasmic disorder, and male orgasmic disorder as defined in Diagnostic and Statistical Manual of Mental Disorders, Fourth Edition, (DSM-IV), American Psychiatric Association, Washington D.C., 1994 as well as the DSM-IV Guidebook, American Psychiatric Press, Inc., Washington D.C., 1995. These definitions of the particular disease states are as they were defined in 1994 and 1995. The five "sexual disturbances" are still defined the same today. In the future, the terms for these sexual disturbances may change, but one skilled in the art will know and realize the disease states themselves are the same.

Sexual activity includes sexual intercourse with or without orgasm, ejaculation, masturbation and sexual foreplay.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1

(R)-Naproxen Chloride

R-naproxen (260 g), methylene chloride (3.33 kg) and DMF (8.2 ml) are added to a reactor. Oxalyl chloride (191.8 g) is slowly added to this mixture. After addition of the oxalyl chloride, the slurry is stirred at 5 to 10° and then slowly warmed to 20–25°. The resulting mixture is concentrated to remove the methylene chloride, branched octane is added to the concentrate and the mixture is again concentrated. More branched octane is added to the concentrate and the mixture is cooled to 0° and stirred to crystallize. The crystal slurry is filtered, the crystal cake is washed with octane and dried at 20–25° to obtain the title compound.

The filtrate from the first crop is concentrated, branched octane is added and the mixture is cooled and stirred to obtain a second crop of the title compound. The slurry is filtered, the crystal cake is washed with branched octane and dried at 20–25°.

Example 1

1-Benzyl-4H-imidazo[4,5,1-ij]quinolin-2(1H)-one (II)

A mixture of 4H-imidazo[4,5,1-ij]quinolin-2(1H)-one (I, J. Heterocyclic Chem.,19, 837–49 (1982), 1.0 g, 5.8 mmol) in DMF (10 ml) is cooled to 0° and treated with potassium t-butoxide in THF (1.98 M, 3.2 ml, 6.3 mmol) maintaining the reaction temperature at 0°. The resulting mixture is stirred at 0° for 10 minutes. Benzyl bromide (0.73 ml, 6.1 mmol) is then added while maintaining the reaction temperature at 0°. After 1 hr, the mixture is partitioned with methyl t-butyl ether (MTBE) from water followed by several water washes. The MTBE phase is concentrated under reduced pressure. The concentrate is cooled to 0°, filtered and washed two times with 0° MTBE. The product is dried at 50° under reduced pressure with a nitrogen purge to give the title compound, CMR (CDCl$_3$, 100 MHz) L 153.78, 136.44, 128.69, 127.67, 127.60, 126.73, 125.86, 122.90, 122.78, 121.28, 116.92, 116.17, 108.36, 44.95 and 42.37.

Example 2

(5R*,6R*)-1-benzyl-5-bromo-6-hydroxy-5,6-dihydro-4H-imidazo[4,5,1-ij]quinolin-2(1H)-one (III)

1-Benzyl-4H-imidazo[4,5,1-ij]quinolin-2(1H)-one (II, XAMPLE 1, 240 g), acetonitrile (1.086 kg), water (227 ml) and fluoboric acid (48.5%, 13.4 g) are mixed and cooled to 0 to 5°. Dibromantin (163.5 g) is slurried into acetonitrile and is added to the reaction mixture. The reaction is carried out for about 3 hr at 0 to 5°. After the reaction is complete, methyl t-butyl ether is added over about 45 minutes keeping the reaction temperature in the pot below 10°. The slurry is cooled to –10 to –15°, stirred for an hour and then filtered. The product is washed with precooled methyl t-butyl ether, dried with 40° nitrogen to give the title compound, CMR (CDCl$_3$) δ156.0, 137.8, 130.5, 129.6, 129.3, 129.1, 126.6, 123.6, 122.5, 119.6, 110.4, 69.9, 49.6, 47.7, 46.9 and 43.8.

Example 3

(5S,6S)-1-Benzyl-5-bromo-2-oxo-1,2,5,6-tetrahydro-4H-imidazo[4,5,1-ij]quinolin-6-yl (2R)-2-(6-methoxy-2-naphthyl)propanoate (IVA) and (5R,6R)-1-benzyl-5-bromo-2-oxo-1,2,5,6-tetrahydro-4H-imidazo[4,5,1-ij]quinolin-6-yl (2R)-2-(6-methoxy-2-naphthyl)propanoate (IVB)

(5R,6R)-1-Benzyl-5-bromo-6-hydroxy-5,6-dihydro-4H-imidazo[4,5,1-ij]quinolin-2(1H)-one (III, EXAMPLE 2, 143 g), methylene chloride (3,136 g), N-methyl morpholine (100.2 g) and 4-dimethylaminopyridine (497 mg) are added to the reactor and the mixture is cooled to 0 to 5°. (R)-Naproxen chloride (PREPARATION 1, 118.5 g) dissolved in methylene chloride (694 ml) is added to the reactor over about 1 hr and the mixture is stirred at 0 to 5° to complete the reaction. If necessary, additional naproxen chloride is added to complete the reaction. Potassium carbonate solution diluted with water is added to the mixture. The aqueous phase is extracted with methylene chloride and the combined methylene phase is washed with water. The washed mixture is concentrated by vacuum distillation and solvent exchange with ethyl acetate is performed. The concentrate is cooled to –10° and stirred. The crystal slurry is filtered and the crystal cake is washed with precooled methyl t-butyl ether and dried at 50° to give the title compound in solid form, (5S,6S)-1-benzyl-5-bromo-2-oxo-1,2,5,6-tetrahydro-4H-imidazo[4,5,1-ij]quinolin-6-yl (2R)-2-(6-methoxy-2-naphthyl)propanoate (IVA), CMR (CDCl$_3$) δ173.2, 157.8, 153.4, 136.1, 134.6, 133.7, 129.2, 128.8, 127.8, 127.8, 127.6, 127.2, 125.9, 125.9, 125.6, 121.5, 121.4, 119.1, 113.2, 109.0, 105., 105.6, 69.2, 55.3, 45.4, 45.2, 42.5, 41.7 and 18.3.

The undesired isomer, (5R,6R)-1-benzyl-5-bromo-2-oxo-1,2,5,6-tetrahydro-4H-imidazo[4,5,1-ij]quinolin-6-yl (2R)-2-(6-methoxy-2-naphthyl)propanoate (IVB) is in the filtrate and can be recovered by means well known to those skilled in the art, (5R,6R)-1-benzyl-5-hydroxy-6-(methylamino)-5,6-dihydro-4H-imidazo[4,5,1-ij]quinolin-2(1H)-one, CMR 173.2, 157.9, 153.4, 136.1, 135.0, 133.8, 129.2, 128.9, 128.8, 127.8, 127.6, 127.4, 125.8, 125.8, 125.7, 121.6, 121.5, 119.3, 113.1, 109.1, 105.7,68.7, 55.3, 45.3, 45.2, 42.2, 41.3 and 18.1 δ.

Example 4

(5R,6R)-1-benzyl-5-hydroxy-6-(methylamino)-5,6-dihydro-4H-imidazo[4,5,1-ij]quinolin-2(1H)-one (V)

(5S,6S)-1-Benzyl-5-bromo-2-oxo-1,2,5,6-tetrahydro-4H-imidazo[4,5,1-ij]quinolin-6-yl (2R)-2-(6-methoxy-2-naphthyl)propanoate (IVA, EXAMPLE 3, 110 g) is slurried in acetonitrile (1,297 g). After adding aqueous methylamine (40 wt %, 327 g) the reaction is carried out for about 12 hr at about 300. After the reaction is complete, the mixture is concentrated and ethyl acetate is added. Dilute hydrochloric acid is added to make the water-soluble salt of the title compound. The byproduct (R-naproxen acetamide impurity) is insoluble in water and stays in the ethyl acetate phase. Further extractions and washes are carried out for better separation of the (naproxen acetamide) impurity with minimum loss of the desired product. Then a sodium hydroxide solution is added to the aqueous phase and the hydrochloride salt of the title compound is converted to the free base. The free base is less soluble in water and is extracted into ethyl acetate. The product mixture is concentrated and solvent exchanged with ethyl acetate to remove water. Crystallization is performed by adding branched chain octane and cooling the mixture. The resulting slurry is filtered, washed and dried at 50° to give the title compound, CMR (CDCl$_3$) δ153.7, 136.3, 128.7, 127.8, 127.7, 125.7, 121.3, 119.9, 118.6, 107.5, 66.2, 60.1, 45.1, 42.6 and 34.0.

Example 5

(7aS,8aR)-4-benzyl-8-methyl-7,7a,8,8a-tetrahydroazireno[2,3-c]imidazo[4,5,1-ij]quinolin-5(4H)-one (VI)

5R,6R)-1-benzyl-5-hydroxy-6-(methylamino)-5,6-dihydro-4H-imidazo[4,5,1-ij]quinolin-2(1H)-one (V, EXAMPLE 4, 70 g) and THF (1,389 g) is concentrated to remove any moisture with distillate as a precaution due to reactivity of n-butyl lithium towards water. The mixture is cooled to about –10° and n-butyllithium is added to make the lithium salt of the starting material with formation of n-butane byproduct in an exothermic reaction. Benzene sulfonyl chloride is added slowly to make benzene sulfonate in an exothermic reaction. The reaction mixture is warmed to 20–25° to complete the reaction. Agueous potassium carbonate solution is added to scavenge the benzene sulfonic acid and the mixture is stirred to allow crystallization. Water is added to complete crystallization, the slurry is stirred, cooled and filtered. The crystal cake is washed with water followed by branched chain octane and dried at 40 to 50° to give the title compound, CMR (CDCl$_3$) δ154.1, 136.3, 128.6, 127.9, 127.6, 124.3, 120.7, 119.7, 107.4, 46.7, 44.9, 40.7, 38.1 and 37.6.

Example 6

(5R)-(methylamino)-5,6-dihydro-4H-imidazo[4,5,1-ij]quinolin-2(1H)-one (VII)

A mixture of (7aS,8aR)-4-benzyl-8-methyl-7,7a,8,8a-tetrahydroazireno[2,3-c]imidazo[4,5,1-ij]quinolin-5(4H)-one (VI, EXAMPLE 5, 40 g) t-amyl alcohol (42.4 g) and anhydrous ammonia (1,200 g) is treated with lithium at ×33°. After the lithium addition is complete, the reaction mixture changes from a yellow slurry to a dark blue mixture. This dark blue mixture is stirred for 30–60 minutes and then quenched with the addition of water. The cooling is removed from the condenser and the ammonia is allowed to evaporate. The residue is dissolved in methanol. This mixture is then concentrated to dryness to give the title compound, which is carried on directly to the next step without isolation.

Example 7

(5R)-(methylamino)-5,6-dihydro-4H-imidazo[4,5,1-ij]quinolin-2(1H)-one (Z)-2-butenedioate (1:1) (VIII)

(5R)-(methylamino)-5,6-dihydro-4H-imidazo[4,5,1-ij]quinolin-2(1H)-one (VII, EXAMPLE 6, 28.0 g) is dissolved in water and the pH is adjusted to 10 with the addition of hydrochloric acid. The mixture is applied in portions to an XAD-16 resin column which is eluted first with water and then with ethanol. The inorganic salts are eluted from the column first with the desired product eluted with the ethanol. The ethanol eluate from the column is treated with maleic acid and the water level is lowered through azeotropic distillation of the ethanol. The precipitated product is isolated by filtration, rinsed with ethyl acetate and dried to give the title compound, CMR (DMSO-d$_6$) δ167.6, 153.9, 136.4, 127.1, 121.5, 119.6, 114.1, 107.5, 51.9, 31.3 and 26.5.

Example 8

(5R)-5-(Methylamino)-5,6-dihydro-4H-imidazo[4,5,1-ij]quinoline-2(1H)-thione

A mixture of (5R)-(methylamino)-5,6-dihydro-4H-imidazo[4,5,1-ij]quinolin-2(1H)-one (VII, EXAMPLE 6, 15.0 g, 73.8 mmol) and tetraphosphorus decasulfide (36.1 g, 81.2 mmol) in pyridine (300 mL) is heated in a 125° oil bath under nitrogen. The reaction is stirred for 5 hr. The mixture is cooled to 20–25° and the pyridine is removed under reduced pressure. Sodium hydroxide (2.2 N, 200 mL) is added. Sodium hydroxide (1 N) is then added. The mixture is saturated with sodium chloride and extracted with methylene chloride (2.5 L, in portions). The organic phase is absorbed onto silica gel (40 g) and purified via column chromatography (silica gel; 225 g; methanol/methylene chloride, 3.5–5.0/96.5–95) to give a solid. Recrystallization of this material from methanol/ethyl acetate/hexanes give the title compound, mp=210–213°; IR (drift) 2940, 2907, 2884, 1483, 1458, 1391, 1366, 1354, 1254, 1239, 1229, 895, 762, 734, 630 cm$^{-1}$; NMR (300 MHz, CDCl$_3$) 7.12, 7.03, 7.00, 4.30, 3.96, 3.30–3.50, 3.15, 2.88 and 2.57 δ; MS (EI, m/z) 219 (M$^+$), 190, 189, 187, 186, 164, 163, 155, 145; HRMS (FAB) calculated for C$_{11}$H$_{13}$N$_3$S (MH$^+$)=220.0908, found 220.0904.

Example 9

(5R)-5-(Methylamino)-5,6-dihydro-4H-imidazo[4,5,1-ij]quinoline-2(1H)-thione malate A mixture of maleic acid (0.317 g, 2.36 mmol) in a minimal amount of methanol (~1 mL) is added to a mixture of (5R)-5-(methylamino)-5,6-dihydro-4H-imidazo[4,5,1-ij]quinoline-2(1H)-thione (EXAMPLE 8, 0.493 g, 2.25 mmol) in methylene chloride. The resulting solid is collected by filtration to give the title compound, mp=195–196°; $[\alpha]^{25}_D$=−60° (c 0.93, methanol); IR (drift) 3140, 3112, 3060, 2969, 1627, 1619, 1568, 1481, 1455, 1398, 1389, 1361, 1220, 868 and 747 cm$^{-1}$; NMR (300 MHz, CD$_3$OD) 7.20–7.30, 7.10–7.20, 6.26, 4.49, 4.31, 4.05–4.20, 3.47, 3.28 and 2.83 δ; CMR (100 MHz, DMSO-d$_6$+CD$_3$OD) 170.4, 169.4, 136.6, 131.1, 130.9, 125.1, 122.1, 116.2, 109.6, 53.9, 43.1, 31.9 and 27.2 δ; MS (ESI, m/z) 220.1 (MH$^+$).

Example A

Hypoactive Sexual Desire Disorder in a Female Patient

A 44 kg, 24 year old female patient is referred by her psychologist for evaluation for and medical treatment of hypoactive sexual desire disorder. The patient recently began to co-habitate with a 28 year old man. She consulted a clinical psychologist because of distress over frequent arguments with her partner. These arguments concern her frustration that her partner is unwilling to marry her and the partner's accusations that she is sexually unresponsive and "boring in bed." The patient reports that although she desires to continue the relationship, she has little or no interest in sexual activity with this partner. The partner initiates all sexual activity in the relationship and she complies so that the relationship will continue. She states that her partner desires sexual intercourse about once per day. Occasionally, the couple's frequency of sexual intercourse is as much as twice per day. She reports that she does not have sexual fantasies since the present relationship began. The patient had a previous relationship with a man that lasted 3 years and involved sexual activity that she found sexually exciting and satisfying. The patient has recently had a physical examination by her family physician, the findings of which were unremarkable. She currently takes no prescription drugs other than low dose birth control pills. She does not routinely use over-the-counter medications or alcohol and denies taking drugs of abuse. The patient is diagnosed as having Hypoactive Sexual Desire Disorder of acquired onset due to situational factor (Diagnostic and Statistical Manual of Mental Disorders, Fourth Edition, 1994). (5R)-(methylamino)-5,6-dihydro-4H-imidazo[4,5,1-ij]quinolin-2(1H)-one (Z)-2-butenedioate (1:1) is prescribed at 1 mg/dose to be taken 0.5 hr before the patient intends to engage in sexual activity. The patient is instructed that she may use the drug on a daily basis, if she and her partner desire sexual activity at this frequency. She is also instructed that on occasions she may use the drug twice in a single day if this is the intended frequency of intercourse. The patient is examined after one month. She reports that she uses the drug once, and occasionally twice, per day. She reports that she has sexual fantasies on 3–4 occasions per week, occasionally initiates sexual activity with her partner, and enjoys an improved sexual relationship with her partner. She also reports that she and her partner argue less frequently and that her partner no longer accuses her of being disinterested in sexual relations. The patient is instructed to continue using the drug.

Example B

Female Sexual Arousal Disorder in a Female Patient

A 64 kg, 22 year old female patient is complaining of vaginal dryness and mild discomfort during sexual intercourse. The patient recently began a relationship with a 35 year old man. Her partner complained of her vaginal dryness and poor vaginal expansion during sexual intercourse. Her partner has made several comments about this during the previous two months and the patient is concerned that her partner is dissatisfied with her lack of sexual responsiveness and may end the relationship. The patient reports that she desires to continue the relationship. The patient has had several previous sexual relationships. She reports that vaginal dryness and some discomfort with vaginal intercourse has occurred during her past sexual relationships. On questioning, she indicates that she has little or no sense of sexual arousal during intercourse. The patient indicates that she has sexual fantasies several times per week. She finds her current partner attractive and sexual desirable. She indicates that she masturbates approximately once per week. During these episodes she usually has an orgasm. Lubrication is not a problem when she masturbates. The patient has recently had a physical examination by her family physician, the findings of which were unremarkable. She currently takes no prescription drugs other than low dose birth control pills. She does not routinely use over-the-counter medications or alcohol and denies taking drugs of abuse. The patient is diagnosed as having Female Sexual Arousal Disorder that is situational due to psychological factors (Diagnostic and Statistical Manual of Mental Disorders, Fourth Edition, 1994). (5R)-(methylamino)-5,6-dihydro-4H-imidazo[4,5,1-ij]quinolin-2(1H)-one (Z)-2-butenedioate (1:1) is prescribed at 3 mg/dose to be taken 0.5–1 hr before the patient intends to engage in sexual activity. The patient is instructed that she may use the drug on a daily basis, if this is the intended frequency of sexual activity. The patient is examined after one month. She reports that she uses the drug prior to intercourse. She reports that vaginal dryness is no longer a problem and that she no longer has pain during initiation of vaginal penetration by her partner. She enjoys an improved sexual relationship with her partner. The patient is instructed to continue using the drug.

Example C

Male Erectile Disorder

A 75 kg, 56 year old male patient has been married for 20 years. He presents complaining that for the past six months he has had difficulty maintaining an erection until completion of sexual intercourse. He develops an adequate erection at the beginning of sexual activity but detumescence occurs when he attempts penetration. His wife is his only current sexual partner. He reports that his wife is patient and understanding of his problem but that he is embarrassed, feels that he is a failure, and is growing progressively more angry and sad about his inability to maintain an erection. He masturbates approximately twice each month. During masturbation, he is usually able to maintain an erection until he ejaculates. The patient has recently had a physical examination by his family physician. The only remarkable findings were a supine diastolic blood pressure 94 mm mercury and a total plasma cholesterol level of 230 mg/dl. He was instructed to follow the American Heart Association dietary recommendations and to reduce his body weight by 5 kg. He currently takes no prescription drugs. He does not routinely use over-the-counter medications or alcohol and denies taking drugs of abuse. The patient is diagnosed as having Male Erectile Disorder that is acquired and situational. The etiology is most likely due to psychological factors, although combined factors, e.g., mild hypertension or atherosclerosis, may contribute (Diagnostic and Statistical Manual of Mental Disorders, Fourth Edition, 1994). (5R)-(methylamino)-5,6-dihydro-4H-imidazo[4,5,1-ij]quinolin-2(1H)-one (Z)-2-butenedioate (1:1) is prescribed at 3 mg/dose to be taken 0.5 hr before the patient intends to engage in sexual activity. The patient is instructed that he may use the drug on a daily basis, if this is the intended frequency of sexual activity. The patient is examined after one month. He reports that he uses the drug prior to intercourse. He reports that he maintains an erection for a satisfactory period after vaginal penetration in almost every attempt at intercourse. He usually experiences intra-vaginal ejaculation. The patient and his wife consider the quality of their sexual relationship to be markedly improved. The patient is instructed to continue using the drug.

Example D

Female Orgasmic Disorder

A 50 kg, 22 year old female patient who married three months before presenting for treatment. She complains that she does not have an orgasm during sexual activity with her husband even though she enjoy the experience and become sexually excited during intercourse. She was not sexually active prior to marriage. She reports that her husband had multiple premarital partners and that he reports all his past partners had orgasms. The patient is upset by her inability to have orgasms and feels she is an poor wife. On questioning she reports that she is "too fat" although her weight is appropriate for her height. She does not masturbate. The patient has recently had a physical examination by her family physician, the findings of which were unremarkable. She currently takes no prescription drugs other than low dose birth control pills. She does not routinely use over-the-counter medications or alcohol and denies taking drugs of abuse. The patient is diagnosed as having Female Orgasmic Disorder that is situational due to psychological factors (Diagnostic and Statistical Manual of Mental Disorders, Fourth Edition, 1994). (5R)-(methylamino)-5,6-dihydro-4H-imidazo[4,5,1-ij]quinolin-2(1H)-one (Z)-2-butenedioate (1:1) is prescribed at 1 mg/dose to be taken about 0.5 hr before the patient intends to engage in sexual activity. The patient is instructed that she may use the drug on a daily basis, if this is the intended frequency of sexual activity. The patient is examined after two months. She reports that she uses the drug prior to intercourse. She reports that she has an orgasm during sexual intercourse on most occasions. She enjoys an improved sexual relationship with her partner. It is recommended that the patient continue to use the drug for an additional six months, then stop taking the drug for a period of two weeks to determine whether she might now be able to have orgasms in the absence of drug therapy.

Example E

Male Orgasmic Disorder

A 80 kg, 40 year old man has been married for 15 years. He presents complaining that he has begun to have difficulty achieving an orgasm during vaginal intercourse with his wife. On most occasions he is unable to ejaculate during sexual intercourse. Infrequently, he is able to ejaculate during sexual, but only after very prolonged vaginal intercourse. He indicates that this has been occurring for at least three months and that he is frustrated and angry about the situation. His further reports that his wife finds the prolonged intercourse that he requires to ejaculate uncomfortable and has begun avoiding sexual relations. He reports that he ejaculate normally when he masturbates. The patient has recently had a physical examination by his family physician, the findings of which were unremarkable. He currently takes no prescription drugs. He does not routinely use over-the-counter medications or alcohol and denies taking drugs of abuse. The patient is diagnosed as having Male Orgasmic Disorder that is acquired and situational due to psychological factors (Diagnostic and Statistical Manual of Mental Disorders, Fourth Edition, 1994). (5R)-(methylamino)-5,6-dihydro-4H-imidazo[4,5,1-ij]quinolin-2(1H)-one (Z)-2-butenedioate (1:1) is prescribed at 3 mg/dose to be taken 0.5–1 hr before the patient intends to engage in sexual activity. The patient is instructed that he may use the drug on a daily basis, if this is the intended frequency of sexual activity. The patient is examined after one month. At this visit he reports that he now ejaculates during vaginal intercourse on all occasions. The patient and his wife consider the quality of their sexual relationship to be markedly improved. The patient is instructed to continue using the drug.

Example F

Mating of Animals of Commercial Value

An adult male Giant Panda on temporary loan from a foreign zoo is desired to have breed to an adult female Giant Panda which is normally resident at the zoo. Because of the commercial value of a potential off-spring it is desirable that the animals mate during the time the adult male is on loan. Both animals are sexually inexperienced and do not engage in intercourse during a two week period. As an alternative to anesthetizing the animals for a facilitated transfer of semen between the animals, the male and female Giant Pandas have (5R)-(methylamino)-5,6-dihydro-4H-imidazo[4,5,1-ij]quinolin-2(1H)-one (Z)-2-butenedioate (1:1) added to their diet on one occasion. The concentration of drug in the diet is calculated to deliver 0.05 mg of free base equivalents of (5R)-(methylamino)-5,6-dihydro-4H-imidazo[4,5,1-ij]quinolin-2(1H)-one (Z)-2-butenedioate (1:1) per kilogram of body weight. One hour after ingesting the diet containing drug, the animals engage in sexual intercourse. A pregnancy and subsequent birth of an off-spring results from this intercourse.

Example G

Reduced Sexual Function in a Male with Idiopathic Epilepsy

A 40 year old, 75 kg male patient has idiopathic epilepsy. He first presented with primary generalized seizures at age 15 years and was diagnosed with idiopathic epilepsy. He has been treated with carbamazepine since age 20. Currently he receives 500 mg/day of the drug. He has had two tonic-clonic seizures during the preceding year. The patient complains of diminished sexual interest in his wife of 8 years. On those occasions when he attempts sexual intercourse, he is able to maintain an erection sufficient for intercourse one-third of the time. He indicates that this problem has had a gradual onset over the previous 5 years. He reports that he rarely has sexual fantasies and rarely masturbates. The patient has recently had a physical examination by his family physician, the findings of which were unremarkable. He currently takes no prescription drugs other than carbamazepine. He does not routinely use over-the-counter medications or alcohol and denies taking drugs of abuse. A penile injection test with Caverject™ Injection results in a normal erection and duplex Doppler ultrasonography indicates an intact vascular system. Plasma testosterone and sex hormone binding globulin assays are performed. The plasma testosterone level is 25 nM, which is considered normal. The plasma sex hormone binding globulin level is 55 nM, which is considered elevated compared to the normal range. The patient is diagnosed with hypogonadism, secondary to chronic carbamazepine treatment (Epilepsia 36: 366–370, 1995). (5R)-(methylamino)-5,6-dihydro4H-imidazo[4,5,1-ij]quinolin-2(1H)-one (Z)-2-butenedioate (1:1) is prescribed at 3 mg/dose to be taken 0.5 hr before the patient intends to engage in sexual activity. The patient is instructed that he may use the drug on a daily basis, if this is the intended frequency of sexual activity. The patient is examined after one month. He reports that he take the drug 2–3 times per week. After taking the drug, he feels more interest in sex and usually initiates sexual activity with his wife. He reports that enjoys a normal sexual relationship. The patient is instructed to continue with the treatment.

Example H

Reduced Sexual Function in a Male Patient with Erectile Dysfunction and Hypoactive Sexual Desire Disorder A 55 year old, 70 kg, male patient is apparently in good health. He presents complaining of a loss of sexual desire and frequent erectile dysfunction since taking an executive position in his company, six weeks previously. He reports that he works long hours and feels a high degree of pressure associated with his job. He is frustrated and angry that when he takes time off from work he is unable to have an intimate relationship with his wife. He reports that although he is periodically interested in initiating sexual relations, on most occasions he is unable to maintain a high level of interest sufficiently long to initiate or to adequately respond to his wife's initiating sexual activity. He further indicates that for the past six months, he has had difficulty maintaining an erection until completion of sexual intercourse. He develops a semi-rigid erection at the beginning of sexual activity but detumescence occurs when he attempts penetration. He reports that he has few erotic fantasies. He has not masturbated for the past several months. He attributes this to a lack of motivation and interest. The patient has recently had a physical examination by his family physician, the findings of which were unremarkable. He does not routinely use over-the-counter medications or alcohol and denies taking drugs of abuse. (5R)-(methylamino)-5,6-dihydro-4H-imidazo[4,5,1-ij]quinolin-2(1H)-one (Z)-2-butenedioate (1:1), 3 mg/dose, and sildenafil (VIAGRA Tablets), 50 mg/dose, are both prescribed. Each is to be taken orally about 0.5 hr before the patient intends to engage in sexual activity. The patient is instructed that he may use the drug combination on a daily basis, if this is the intended frequency of sexual activity. The patient is examined after one month. He reports that he takes the drug combination 2–3 times per week. After taking the drug combination he feels motivated to initiate sexual activity, readily has sexual fantasies that are sustained during sexual intercourse, and has no difficulty maintaining an erection to completion of sexual intercourse. He reports that he enjoys an improved sexual relationship with his partner. The patient is advised to continue taking the (5R)-(methylamino)-5,6-dihydro-4H-imidazo[4,5,1-ij]quinolin-2(1H)-one (Z)-2-butenedioate (1:1) for another six months as he adapts to the situational stress associated with his new job. After this time he is advised to stop taking the drug for a period of two weeks to determine whether his sexual motivation and desire have returned to the level he enjoyed prior to the change in jobs.

Example I

Hypoactive Sexual Desire Disorder in a Female Patient

Following the general method of treatment of EXAMPLE A and making non-critical variations but using (5R)-5-(methylamino)-5,6-dihydro-4H-imidazo[4,5,1-ij]quinoline-2(1H)-thione in place of (5R)-(methylamino)-5,6-dihydro-4H-imidazo[4,5,1-ij]quinolin-2(1H)-one (Z)-2-butenedioate (1:1) the same positive treatment effect is obtained.

Example J

Female Sexual Arousal Disorder in a Female Patient

Following the general method of treatment of EXAMPLE B and making non-critical variations but using (5R)-5-(methylamino)-5,6-dihydro-4H-imidazo[4,5,1-ij]quinoline-2(1H)-thione in place of (5R)-(methylamino)-5,6-dihydro-4H-imidazo[4,5,1-ij]quinolin-2(1H)-one (Z)-2-butenedioate (1:1) the same positive treatment effect is obtained.

Example K

Male Erectile Disorder

Following the general method of treatment of EXAMPLE C and making non-critical variations but using (5R)-5-(methylamino)-5,6-dihydro-4H-imidazo[4,5,1-ij]quinoline-2(1H)-thione in place of (5R)-(methylamino)-5,6-dihydro-4H-imidazo[4,5,1-ij]quinolin-2(1H)-one (Z)-2-butenedioate (1:1) the same positive treatment effect is obtained.

Example L

Female Orgasmic Disorder

Following the general method of treatment of EXAMPLE D and making non-critical variations but using (5R)-5-(methylamino)-5,6-dihydro-4H-imidazo[4,5,1-ij]quinoline-2(1H)-thione in place of (5R)-(methylamino)-5,6-dihydro-4H-imidazo[4,5,1-ij]quinolin-2(1H)-one (Z)-2-butenedioate (1:1) the same positive treatment effect is obtained.

Example M

Male Orgasmic Disorder

Following the general method of treatment of EXAMPLE E and making non-critical variations but using (5R)-5-(methylamino)-5,6-dihydro-4H-imidazo[4,5,1-ij]quinoline-2(1H)-thione in place of (5R)-(methylamino)-5,6-dihydro-4H-imidazo[4,5,1-ij]quinolin-2(1H)-one (Z)-2-butenedioate (1:1) the same positive treatment effect is obtained.

Example N

Mating of Animals of Commercial Value

Following the general method of treatment of EXAMPLE F and making non-critical variations but using (5R)-5-(methylamino)-5,6-dihydro-4H-imidazo[4,5,1-ij]quinoline-2(1H)-thione in place of (5R)-(methylamino)-5,6-dihydro-4H-imidazo[4,5,1-ij]quinolin-2(1H)-one (Z)-2-butenedioate (1:1) the same positive treatment effect is obtained.

Example O

Reduced Sexual Function in a Male with Idiopathic Epilepsy

Following the general method of treatment of EXAMPLE G and making non-critical variations but using (5R)-5-(methylamino)-5,6-dihydro-4H-imidazo[4,5,1-ij]quinoline-2(1H)-thione in place of (5R)-(methylamino)-5,6-dihydro-4H-imidazo[4,5,1-ij]quinolin-2(1H)-one (Z)-2-butenedioate (1:1) the same positive treatment effect is obtained.

Example P

Reduced Sexual Function in a Male Patient with Erectile Dysfunction and Hypoactive Sexual Desire Disorder Following the general method of treatment of EXAMPLE H and making non-critical variations but using (5R)-5-(methylamino)-5,6-dihydro-4H-imidazo[4,5,1-ij]quinoline-2(1H)-thione in place of (5R)-(methylamino)-5,6-dihydro-4H-imidazo[4,5,1-ij]quinolin-2(1H)-one (Z)-2-butenedioate (1:1) the same positive treatment effect is obtained.

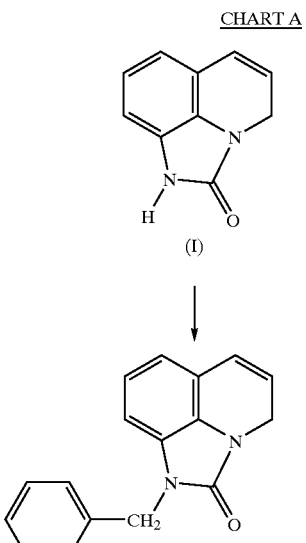

CHART A

-continued

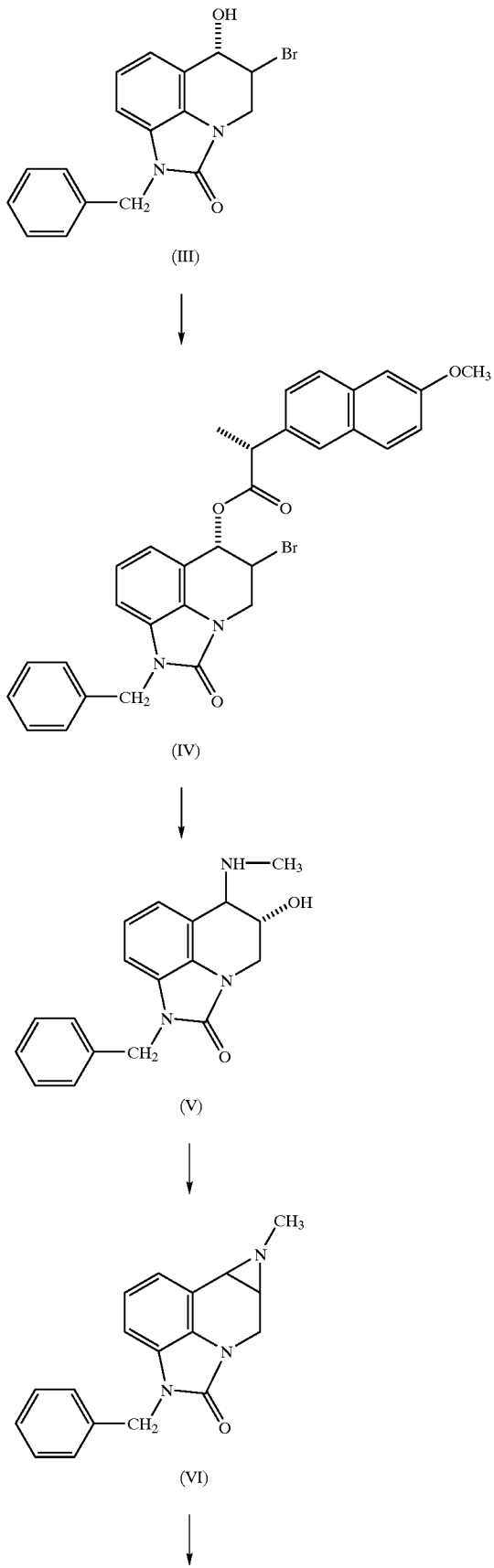

-continued

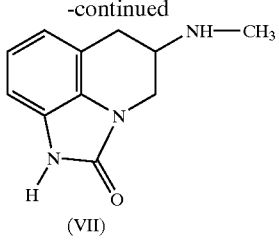

(VII)

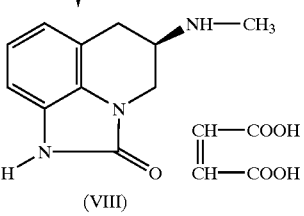

(VIII)

What is claimed is:
1. A method of treating male erectile disorder in a male human, who is in need of such treatment, which comprises oral administration in a single daily dose of from about 0.5 thru about 5 mg of a compound selected from the group consisting of:

(5R)-(methylamino)-5,6-dihydro-4H-imidazo[4,5,1-ij] quinolin-2(1H)-one and
(5R)-5-(methylamino)-5,6-dihydro-4H-imidazo[4,5,1-ij] quinoline-2(1H)-thione and pharmaceutically acceptable salts thereof to the human.

2. A method of treating male erectile disorder according to claim 1 where the compound (5R)-(methylamino)-5,6-dihydro-4H-imidazo[4,5,1-ij]quinolin-2(1H)-one.

3. A method of treating male erectile disorder according to claim 2 where the compound is (5R)-(methylamino)-5,6-dihydro-4H-imidazo[4,5,1-ij]quinolin-2(1H)-one (Z)-2-butenedioate (1:1).

4. A method of treating male erectile disorder according to claim 1 where the compound of formula (A) is (5R)-5-(methylamino)-5,6-dihydro-4H-imidazo[4,5,1-ij]quinoline-2(1H)-thione.

5. A method of treating male erectile disorder according to claim 1 where the pharmaceutically acceptable salt is selected from the group consisting of salts of the following acids methanesulfonic, hydrochloric, hydrobromic, sulfuric, phosphoric, nitric, benzoic, citric, tartaric, fumaric, maleic, $CH_3-(CH_2)_n-COOH$ where n is 0 thru 4, $HOOC-(CH_2)_n-COOH$ where n is as defined above.

6. A method of treating male erectile disorder according to claim 1 where the amount of the compound is from about 1 thru about 3 mg/person/dose.

7. A method of treating male erectile disorder according to claim 1 where the compound is administered from about 10 minutes to about 8 hr prior to sexual activity.

8. A method of treating male erectile disorder according to claim 7 where the compound is administered from about 0.5 hr to about 1 hr prior to sexual activity.

9. A method of treating male erectile according to claim 8 where the compound is administered about 0.5 hr prior to sexual activity.

10. A method of treating male erectile according to claim 1 where the human does not have Parkinson's disease.

11. A method of treating male erectile according to claim 1 where the human does not experience postural hypotension.

12. A method of treating male erectile according to claim 1 where the compound is used in combination with a sexually effective amount of one or more vascular smooth muscle relaxation agents where both the compound is administered within 8 hours prior to sexual activity and the vascular smooth muscle relaxation agent is administered to the human within a sexually effective time period prior to sexual activity.

13. A method of treating male erectile according to claim 12 where the vascular smooth muscle relaxation agents is selected from the group consisting of phosphodiesterase type 5 inhibitors, phosphodiesterase type 3 inhibitors, non-selective phosphodiesterase inhibitors, nitric oxide donor drugs, alpha type 1 adrenergic receptor antagonists, alpha type 2 adrenergic receptor antagonists, prostaglandin E1 receptor agonists (PGE1) and vasoactive intestinal polypeptide (VIP) agents.

14. A method of treating male erectile according to claim 13 where the vascular smooth muscle relaxation agents is selected from the group consisting of sildenafil, ICOS-351, milrinone, papaverine, linsidomine, phentolamine, yohimbine, prostaglandin E1 (PGE1) and VIP.

* * * * *